US009144405B2

United States Patent
Kim et al.

(10) Patent No.: US 9,144,405 B2
(45) Date of Patent: Sep. 29, 2015

(54) USER HEALTH MONITORING SYSTEM COMPRISING 3D GLASSES AND DISPLAY APPARATUS, AND DISPLAY APPARATUS AND CONTROL METHOD THEREOF

(75) Inventors: Kwang-soo Kim, Seoul (KR); Do-sung Jung, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 595 days.

(21) Appl. No.: 13/542,314

(22) Filed: Jul. 5, 2012

(65) Prior Publication Data

US 2013/0057660 A1    Mar. 7, 2013

(30) Foreign Application Priority Data

Sep. 2, 2011  (KR) .................. 10-2011-0089120

(51) Int. Cl.
| | |
|---|---|
| H04N 13/04 | (2006.01) |
| A61B 5/00 | (2006.01) |
| A61B 5/024 | (2006.01) |
| A61B 5/0476 | (2006.01) |
| A61B 5/0488 | (2006.01) |
| G02C 1/00 | (2006.01) |

(52) U.S. Cl.
CPC ............. *A61B 5/743* (2013.01); *A61B 5/02416* (2013.01); *A61B 5/0476* (2013.01); *A61B 5/0488* (2013.01); *A61B 5/6803* (2013.01)

(58) Field of Classification Search
CPC .......... H04N 13/0497; H04N 13/0404; H04N 13/0409; H04N 13/0422; G02B 27/2214
USPC ......................................................... 348/51
See application file for complete search history.

(56) References Cited

U.S. PATENT DOCUMENTS

| | | | |
|---|---|---|---|
| 6,864,910 B1* | 3/2005 | Ogino et al. | 348/42 |
| 7,255,437 B2* | 8/2007 | Howell et al. | 351/158 |
| 7,376,238 B1* | 5/2008 | Rivas et al. | 381/381 |
| 7,543,934 B2* | 6/2009 | Howell et al. | 351/158 |
| 8,180,185 B2* | 5/2012 | Xia et al. | 385/12 |
| 8,542,326 B2* | 9/2013 | MacNaughton et al. | 349/15 |

(Continued)

FOREIGN PATENT DOCUMENTS

| | | |
|---|---|---|
| EP | 2100556 A1 | 9/2009 |
| WO | 2006121956 A1 | 11/2006 |
| WO | 2007013054 A1 | 2/2007 |

OTHER PUBLICATIONS

Communication dated Nov. 29, 2012 issued by the European Patent Office in counterpart European Patent Application No. 12169373.3.

Primary Examiner — Sath V Perungavoor
Assistant Examiner — Howard D Brown, Jr.
(74) Attorney, Agent, or Firm — Sughrue Mion, PLLC

(57) ABSTRACT

A user health monitoring system having 3D glasses and a display apparatus and a display apparatus and a control method thereof, the user health monitoring system including: 3D glasses which obtain biosignal information of a user and transmit; and a display apparatus which receives the biosignal information transmitted by the 3D glasses, obtains a health index of the user by using the biosignal information and controls a display state according to the health index. With this configuration, a user's health condition may be monitored in real-time with a biosignal of the user viewing a 3D image and a 3D display state may be controlled according to the user's health condition to thereby protect a user's health.

26 Claims, 6 Drawing Sheets

(56) References Cited

U.S. PATENT DOCUMENTS

| | | |
|---|---|---|
| 2001/0019450 A1* | 9/2001 | Ogino .......................... 359/462 |
| 2003/0063222 A1 | 4/2003 | Creed et al. |
| 2006/0252978 A1* | 11/2006 | Vesely et al. .................... 600/27 |
| 2007/0109491 A1* | 5/2007 | Howell et al. .................. 351/41 |
| 2012/0075168 A1* | 3/2012 | Osterhout et al. ................ 345/8 |
| 2014/0160424 A1* | 6/2014 | Benko et al. .................. 351/158 |
| 2014/0168349 A1* | 6/2014 | Eom et al. .................. 348/14.03 |

* cited by examiner

USER HEALTH MONITORING SYSTEM COMPRISING 3D GLASSES AND DISPLAY APPARATUS, AND DISPLAY APPARATUS AND CONTROL METHOD THEREOF

CROSS-REFERENCE TO RELATED PATENT APPLICATION

This application claims priority from Korean Patent Application No. 10-2011-0089120, filed on Sep. 2, 2011 in the Korean Intellectual Property Office, the disclosure of which is hereby incorporated herein by reference.

BACKGROUND

1. Field

Apparatuses and methods consistent with the exemplary embodiments relate to a user health monitoring system comprising three-dimensional (3D) glasses, a display apparatus, and a control method thereof, and more particularly, to a system which senses and analyzes a user's biosignals through 3D glasses, a display apparatus and an external server to thereby monitor a health condition of a user of a 3D display apparatus.

2. Description of the Related Art

A display apparatus processes an image signal or image data, which is input from the outside or stored therein, by various processes, and displays an image on a panel or a screen. The display apparatus varies by a display method, including a TV, a monitor, a portable media player (PMP), etc. In line with the development of technology, a display apparatus which provides a 3D effect on a screen which is viewed by a user has emerged. Such a display apparatus separately displays a left eye image and a right eye image on a screen by using a difference of a viewing angle between left and right eyes. If a user wears 3D glasses, the left and right eye images overlap each other by refraction of light and a user may see the 3D effect.

If a user wears the 3D glasses and views 3D images for a long time, he/she may feel tired or dizzy or may have other abnormal health conditions because of the difference in the image viewed by each both eye.

However, the conventional 3D display apparatus provides 3D content image without regard to a user's health condition, and may not prevent a user's health problem.

SUMMARY

One or more exemplary embodiments provide a user health monitoring system, a display apparatus and a control method thereof which monitors in real-time a user's health condition with a biosignal of the user viewing a 3D image and controls a 3D display state according to the user's health condition to thereby protect a user's health.

According to an aspect of an exemplary embodiment, there is provided a user health monitoring system including: 3D glasses which obtain biosignal information relating of a user and transmit the biosignal information; and a display apparatus which receives the biosignal information transmitted by the 3D glasses, obtains a health index of the user by using the biosignal information and controls a display state according to the health index.

The 3D glasses may include a pulse sensor which senses pulse information of the user and transmit the sensed pulse information in the biosignal information to the display apparatus.

The 3D glasses may include a pulse sensor which is installed in a temple of the 3D glasses.

The display apparatus may control the display state by at least one of displaying an alarm notification, suspending play of 3D image content, adjusting 3D depth information, converting to a two-dimensional (2D) mode, and recommending image content corresponding to the health index.

The display apparatus may extract pulse information from the biosignal information, and obtain a stress index of the user as the health index, from the pulse information.

The biosignal information may include at least one of pulse information, photoplethysmography (PPG) information, galvanic skin reflex (GSR) information, skin conductivity information, electroencephalogram (EEG) information, facial muscular motion information, and respiration information.

The user health monitoring system may further include an auxiliary electrode which measures at least one of EEG, electromyogram (EMG) and facial muscular motion, the auxiliary electrode may be connected to the 3D glasses, and a measurement result of the auxiliary electrode may be included in the biological signal information transmitted to the 3D glasses.

The user health monitoring system may further include an external server which receives the biosignal information from the display apparatus or the 3D glasses, calculates the health index by analyzing the biosignal information and transmits the health index to the display apparatus.

The user health monitoring system may further include an external server which receives the biosignal information from the display apparatus or the 3D glasses, determines the health index by analyzing the biosignal information and transmits a recommended content list corresponding to the health index to the display apparatus.

The display apparatus may display a real-time health condition of the user as the health index.

According to an aspect of an exemplary embodiment, there is provided a display apparatus including: an image signal receiver which receives an image signal including 3D image content; an image processor which processes the image signal to be displayed; a display unit which displays thereon the 3D image content included in the processed image signal; a biosignal receiver which receives biosignal information of a user sensed by 3D glasses worn by the user to view the 3D image content; and a controller which controls the biosignal receiver to receive the biosignal information, and which obtains the a health index of the user by using the biosignal information and controls a display state of the display unit according to the health index.

The controller may control the display state by at least one of displaying an alarm notification, suspending play of the 3D content, adjusting 3D depth information, converting to a 2D mode, and recommending a content corresponding to the heath index.

The controller may extract pulse information from the biosignal information and obtain a stress index of the user as the health index, from the pulse information.

The biosignal may include at least one of pulse information, PPG information, GSR information, skin conductivity information, EEG information, facial muscular motion information, and respiration information.

The controller may display on the display unit a real-time health condition of the user as the health index.

The controller may control a transmission of the biosignal information to an external server, and a reception of the health index which is determined by analyzing the biosignal information from the external server.

The controller may control a transmission of the biosignal information to an external server and a reception of a recommended content list corresponding to the health index which is determined by analyzing the biosignal information in the external server.

The biosignal receiver may receive the biosignal from the 3D glasses by one of communication methods including Wi-Fi, Bluetooth, Zigbee and ultra wideband (UWB).

According to an aspect of another exemplary embodiment there is provided a control method of a display apparatus, including: receiving an image signal and displaying on a display unit of the display apparatus 3D image content included in the image signal; receiving biosignal information of a user sensed by 3D glasses which are worn by a user to view the 3D image content; obtaining a health index of the user by using the biosignal information; and controlling a display state of the display unit according to the health index.

The controlling the display state may include at least one of displaying an alarm, suspending play of 3D content, adjusting 3D depth information, converting to a 2D mode, and recommending a content corresponding to the health index.

The obtaining the health index may include extracting pulse information from the biosignal information, and obtaining a stress index of the user as the health index from the pulse information.

The biosignal may include at least one of pulse information, PPG information, GSR information, skin conductivity information, EEG information, facial muscular motion information, and respiration information.

The control method may further include displaying on the display unit a real-time health of the user condition as the health index.

The control method may further include transmitting the biosignal information to an external server, and receiving from the external server the health index determined by analyzing the biosignal information.

The control method may further include transmitting the biosignal information to an external server, and receiving from the external server a recommended content list corresponding to the health index determined by analyzing the biosignal information.

The receiving the biosignal information may include receiving the biosignal information from the 3D glasses by one of communication methods including Wi-Fi, Bluetooth, Zigbee and ultra wideband (UWB).

BRIEF DESCRIPTION OF THE DRAWINGS

The above and/or other aspects will become apparent and more readily appreciated from the following description of the exemplary embodiments, taken in conjunction with the accompanying drawings, in which.

DETAILED DESCRIPTION OF EXEMPLARY EMBODIMENTS

Figure 1:
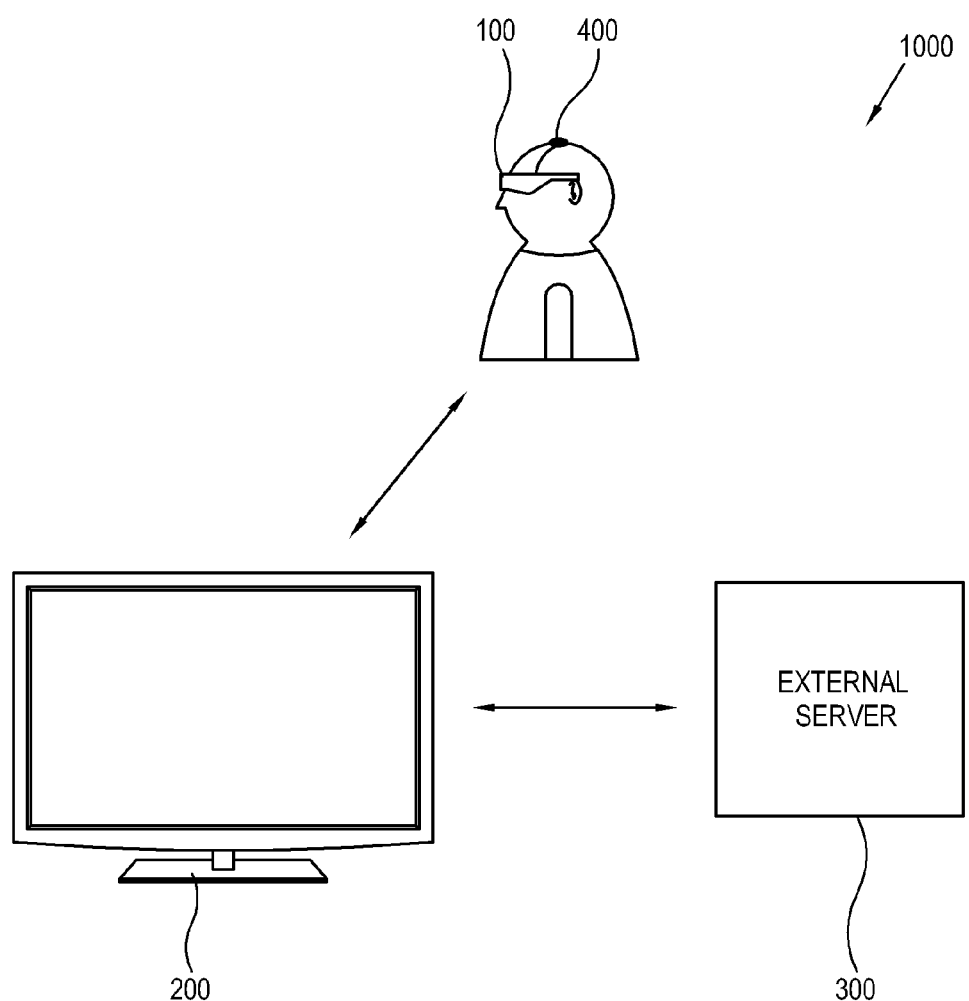
FIG. 1 illustrates a user health monitoring system according to an exemplary embodiment.

Below, exemplary embodiments will be described in detail with reference to accompanying drawings so as to be easily realized by a person having ordinary knowledge in the art.

The exemplary embodiments may be embodied in various forms without being limited to the exemplary embodiments set forth herein. Descriptions of well-known parts are omitted for clarity, and like reference numerals refer to like elements throughout.

FIG. 1 illustrates a user health monitoring system 1000 according to an exemplary embodiment.

As shown therein, the user health monitoring system 1000 according to the present embodiment includes a display apparatus 200 which processes an image signal that is input from the outside, and displays thereon 3D image content included in the image signal, and 3D glasses 100 which are worn by a user to view a 3D image. The display apparatus 200 separately displays a left eye image and a right eye image on a screen, and provides a 3D image as a user wears the 3D glasses 100 and the left and right eye images overlap each other by refraction of light.

The 3D glasses 100 obtain information relating to a user's biosignal, and may transmit the information to the display apparatus 200 or the external server 300 wirelessly or through a wired connection. Details of the 3D glasses 100 according to the present embodiment will be described with reference to FIG. 2.

The display apparatus 200 receives information on the user's biosignal sensed by the 3D glasses 100. In this case, the display apparatus 200 may receive the information on the biosignal from the 3D glasses 100 by one of wireless communication methods including Wi-Fi, Bluetooth, Zigbee and ultra wideband (UWB).

The display apparatus 200 obtains a user's health index by using the received information. The health index may include numerical information such as a pulse rate, photoplethysmography (PPG) and a respiration rate per unit time, and numerical information or normal/abnormal information according to a prestored calculation and analysis algorithm based on the received information. The display apparatus 200 may display a user's real-time health condition as a user's health index.

The display apparatus 200 may extract pulse information from the received information, and obtain a user's stress index as the health index from the pulse information. The pulse rate per unit time may be measured by a known method from the biosignal sensed by the 3D glasses 100, and accordingly the user's stress index is determined. For example, if the pulse rate is high, it means a user is in an excited state and accordingly a user's stress index rises. If the pulse rate is low, it means a user is in a relaxed state and accordingly a user's stress index may fall.

The display apparatus 200 monitors a user's health index which changes before viewing and while viewing a 3D image, and controls a display state according to the obtained health index. For example, if a user's stress index increases while viewing a 3D image, depth information of the 3D image is adjusted and the depth of the 3D is reduced by changing a left eye image and a right eye image of the 3D image. If the stress index decreases, the depth of the 3D image may be increased. Accordingly, a user may view the 3D image in a proper depth according to his/her current stress index, i.e., excitement state, and may maintain a proper excitement state and prevent a safety incident.

For example, if a user's health is determined as abnormal according to a stress index, a text or picture which shows the abnormal health condition or recommends avoiding the viewing and taking a rest may be displayed for a user as an alarm. Otherwise, 3D image content which is viewed by a user may be converted into a two-dimensional (2D) image or, the playing of the 3D image may be automatically ended to force a user to take a rest, or recommendation information on the image content corresponding to a current health index may be displayed.

The user health monitoring system 1000 according to an exemplary embodiment may further include an auxiliary electrode 400 which measures at least one of electroencephalogram (EEG), electromyography (EMG) and facial muscular motion information.

The auxiliary electrode 400 may be connected to the 3D glasses 100 in a wired manner and transmit to the 3D glasses 100 the information on at least one of the EEG, EMG and facial muscular motion information sensed by it. The 3D glasses 100 may transmit the received information to the display apparatus 200, which may analyze the information to obtain the health index and control the display state.

The user health monitoring system 1000 according to an exemplary embodiment may further include an external server 300 which transmits and receives information to/from the display apparatus 200 and to/from the 3D glasses 100. The display apparatus 200 or 3D glasses 100 may be connected to the external server 300 through the Internet or a network, and the external server 300 may be connected to a plurality of display apparatuses.

The external server 300 may receive user's biosignal information from the display apparatus 200 or the 3D glasses 100 and calculate the health index by analyzing the information. The method of receiving the biosignal information and calculating the health index by the external server 300 may be the same as that by the display apparatus 200 according to the present embodiment. In this case, the display apparatus 200 may not need an additional configuration to transmit to the external server 300 the biosignal information transmitted by the 3D glasses 100, analyze the biosignal information and calculate the health index.

The external server 300 may transmit the calculated health index to the display apparatus 200. The display apparatus 200 may control the display state by displaying an alarm, suspending play of the 3D content, adjusting 3D depth information or converting to the 2D mode according to the received health index.

The external server 300 may transmit to the display apparatus 200 a recommended content list corresponding to the calculated health index. As users of a plurality of display apparatuses 200 or 3D glasses 100 transmit the biosignal information to the external server 300, the external server 300 may summarize and analyze any change of the health index before and after viewing 3D content and prepare a recommended content list corresponding to the user's health index. As users may share data on the change of the health index before and after viewing the 3D content through the external server 300, recommended contents according to a user's emotional state may be shared through the web site and social network service (SNS).

Figure 2:
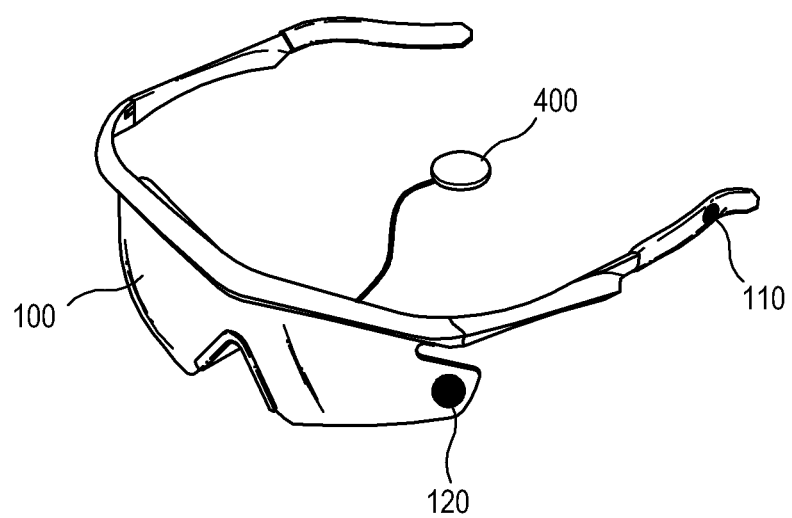
FIG. 2 illustrates 3D glasses of the user health monitoring system according to an exemplary embodiment.

FIG. 2 illustrates the 3D glasses 100 of the user health monitoring system 1000 according to an exemplary embodiment.

The 3D glasses 100 include a biosignal sensor 110 and a communication unit 120 in addition to a rim and lenses. The biosignal sensor 110 may include an electrode for measuring at least one biosignal which senses an electric signal from a user's body, and transmits to the communication unit 120 information on the sensed user's biosignal.

The biosignal sensor 110 may include a pulse sensor which senses user's pulse information, and transmit the sensed pulse information to the display apparatus 200. As an example of sensing a user's pulse by the pulse sensor, the pulse sensor may use the character of hemoglobin in user's blood that absorbs light in a particular wavelength while the light in an infrared band which is output by the pulse sensor passes through the surface of a user's skin and then is reflected to be introduced to an isolated transistor. The number of hemoglobin depends on the hematocele, and accordingly the amount of light introduced to the transistor also varies, and the regular change of the amount of hematocele may be sensed by the transistor and sensed by a sensing voltage of the pulse sensor. The pulse sensor may sense the user's pulse by using other known methods other than the foregoing method.

The pulse sensor may be installed in a temple of the 3D glasses 100. The temple of the 3D glasses 100 contacts a top area of a user's ear when a user wears the 3D glasses 100. As the top of the ear is near the temporal lobe, the pulse sensor may relatively accurately sense the user's pulse from the hematocele of the temporal arteries located in the temporal lobe.

The user's biosignal which is sensed by the biosignal sensor 110 may include pulse, PPG, GSR, skin conductivity, EEG, facial muscular motion information and respiration information. To sense the foregoing, the biosignal sensor 110 may include a PPG electrode, a GSR electrode, an EEG electrode, an EMG electrode, and a microphone electrode to measure respiration.

For example, the PPG electrode may sense a waveform synchronized with the contraction and relaxation of the heart from a capillary of the skin, calculate the amount of hemoglobin from the measurement result of the activity of the heart and estimate the PPG. The GSR electrode may apply a certain voltage between two points of the skin, measure the size of impedance of the skin as a result of the increase in moisture and quantitatively calculate the degree of sensitivity of the human body from the measurement result of the skin response. The microphone may sense the flow of air as sound and estimate a respiration pattern and a respiration rate. Each electrode of the biosignal sensor 110 may be located in different parts of the 3D glasses 100 according to the nature of the biosignal to be measured.

The communication unit 120 receives the sensed user's biosignal information, and transmits the information to the display apparatus 200 in a wireless manner. The communication unit 120 may include a wireless communication module for one of communication methods including Wi-Fi, Bluetooth, Zigbee and ultra wideband (UWB).

Figure 3:
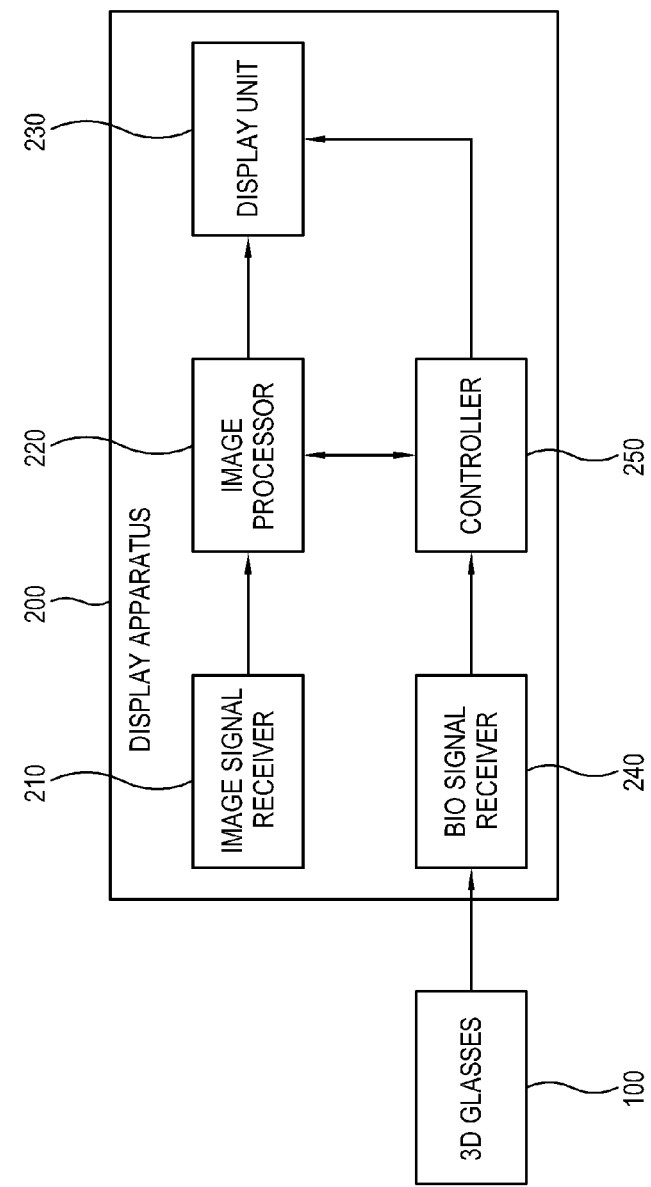
FIG. 3 is a control block diagram of a display apparatus according to an exemplary embodiment.

FIG. 3 is a control block diagram of the display apparatus 200 according to an exemplary embodiment.

The display apparatus 200 according to the present embodiment includes an image signal receiver 210, an image processor 220, a display unit 230, a biosignal receiver 240, and a controller 250. The display apparatus 200 may include a TV or a monitor, but is not limited thereto.

The image signal receiver 210 receives an image signal including 3D image content from an external image supply source (not shown). The image supply source may vary including a computer main body which generates an image signal and provides the image signal to a local network with a CPU and a graphic card, a server which supplies an image signal to a network, a transmission device of a broadcasting station which transmits a broadcasting signal by using airwave or cable. The image signal receiver 210 may receive an image signal from various image supply sources.

The image processor 220 receives an image signal from the image signal receiver 210 and processes the image signal into a form displayable on the display unit 230 (to be described later). If a received image signal includes a 3D image signal, the image processor 220 may process the image signal to display a 3D image from which a left eye image and a right eye image are separated, and adjust a depth of the 3D image according to a control of the controller 250 (to be described later). The image processing performed by the image processor 220 may further include decoding, deinterlacing, converting a frame refresh rate, scaling, reducing noise for improvement of image quality, detail enhancement, line scanning, etc. corresponding to various image formats.

The display unit 230 displays thereon 3D image content included in the image signal, according to a control of the controller 250. The display unit 230 may include a display panel to display an image thereon and a panel driver to display an image on the display panel, and is not limited to exemplary methods. The display unit 230 may further display thereon a health index image, and an alarm display image as well as the image content.

The biosignal receiver 240 receives user's biosignal information measured by the 3D glasses 100 which are used to view 3D image content. The 3D glasses 100 may sense a biosignal of a user who is viewing 3D image content by using the biosignal sensor 110 included in the 3D glasses 100 or the auxiliary electrode 400 connected to the 3D glasses 100 in a wired manner. The sensed biosignal may include pulse, PPG, GSR, skin conductivity, EEG, facial muscular motion information, respiration information, EMG, etc. The exemplary embodiment for sensing the biosignal by the 3D glasses 100 is the same as that which has been described with reference to FIG. 2.

The biosignal receiver 240 may receive the biosignal information from the 3D glasses 100 by one of communication methods including Wi-Fi, Bluetooth, Zigbee and UWB, and include a wireless communication module corresponding to a wireless communication method of the 3D glasses 100.

The controller 250 controls overall operations of the display apparatus 200 according to an exemplary embodiment. The controller 250 may include a control program, a non-volatile memory such as a read only memory (ROM) and a flash memory storing the control program therein, a volatile memory such as a random access memory (RAM) loading at least a part of the stored control program, and a microprocessor such as a micro control unit (MCU) executing the loaded control program.

If 3D image content is displayed on the display unit 230 according to a user's input, the controller 250 may control the biosignal receiver 240 to receive the user's biosignal information, and obtain the user's health index by using the received information. The health index may include numerical information such as a pulse rate, PPG, and a respiration rate per unit time, numerical information or normal/abnormal information according to a prestored calculation and analysis algorithm based on the received information.

The controller 250 may extract pulse information from the received information and obtain a user's stress index as the health index from the pulse information. The pulse rate per unit time may be measured by a known method from the biosignal sensed by the 3D glasses 100, and accordingly the user's stress index is determined. For example, if the pulse rate is high, it means a user is in an excited state and accordingly a user's stress index rises. If the pulse rate is low, it means a user is in a relaxed state and accordingly a user's stress index may fall.

The controller 250 monitors a user's health index which changes before viewing and while viewing a 3D image, and controls a display state according to the obtained health index. For example, if a user's stress index increases while viewing a 3D image, depth information of the 3D image is adjusted and the depth of the 3D is reduced by changing a left eye image and a right eye image of the 3D image. If the stress index decreases, the depth of the 3D may be increased. For example, if a user's health is determined as abnormal according to a stress index, a text or picture which shows the abnormal health condition or recommends avoiding the viewing and taking a rest may be displayed for a user as an alarm. Otherwise, 3D image content which is viewed by a user may be converted into a 2D image, or the playing of the 3D image may be automatically ended to force a user to rest, or recommendation information on the image content corresponding to a current health index may be displayed.

The controller may control a transmission of the biosignal information to the external server 300 and receipt of the health index calculated by the analysis of the information from the external server 300. The method of receiving the biosignal information from the external server 300 and calculating the health index is the same as that which has been described above.

The controller 250 may receive a recommended content list corresponding to the health index from the external server 300. The received recommended content list may be displayed on the display unit 230, and the controller 250 may offer a proper content viewing according to a user's current health condition.

Figure 4:
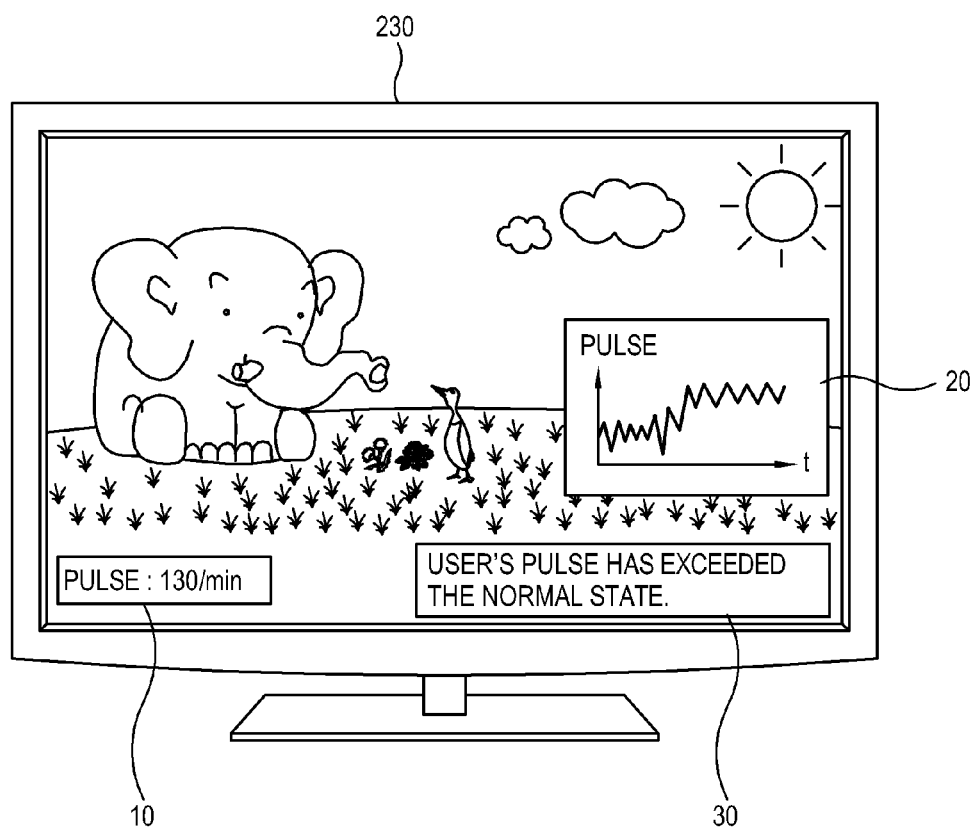
FIG. 4 illustrates a screen displayed on a display unit according to an exemplary embodiment.

FIG. 4 illustrates a screen which is displayed on the display unit 230 according to an exemplary embodiment.

The display unit 230 displays thereon 3D image content according to a control of the controller 250. If the controller 250 obtains a user's health index and controls the display state according to the user's health index, the image displayed on the display unit 230 changes accordingly.

As shown in FIG. 4, the display unit 230 may display thereon a numerical value such as a current pulse rate 10 as a health index, a pulse rate variation graph 20 according to viewing of 3D image content or an alarm message or indicator 30 which warns a user of his/her abnormal health condition if the controller 250 determines that the user's health condition is abnormal based on the health index, according to a control of the controller 250 other than the 3D image content.

Figure 5:
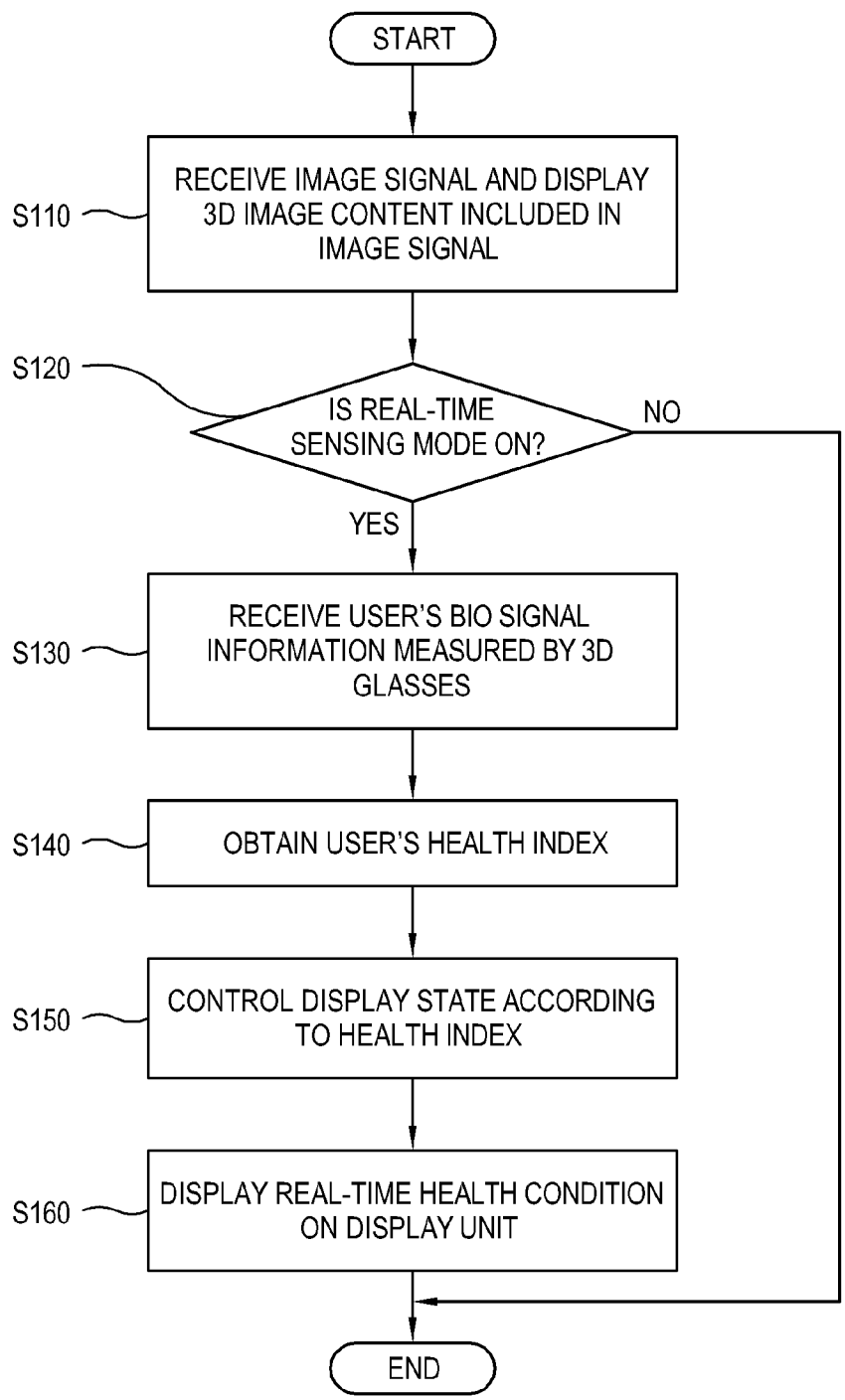
FIG. 5 is a first control flowchart of the display apparatus according to an exemplary embodiment.

FIG. 5 is a first control flowchart of the display apparatus 200 according to an exemplary embodiment.

The display apparatus 200 according to the present exemplary embodiment receives an image signal, and displays 3D image content included in the image signal (S110). A user may wear the 3D glasses 100 to view the 3D image content, and input his/her selection on the sensing of his/her biosignal in real-time while viewing the 3D image content through a button provided in the display apparatus 200 or a remote control device (not shown).

If the real-time sensing mode of the biosignal is set (S120-YES), the display apparatus 200 receives the user's biosignal information measured by the 3D glasses 100 worn by a user (S130). The display apparatus 200 may receive the information from the 3D glasses 100 by one of communication methods including Wi-Fi, Bluetooth, Zigbee and UWB. The method of measuring the user's biosignal by the 3D glasses 100 is the same as that which has been described with reference to FIG. 2.

The display apparatus 200 may obtain the user's health index by using the received user's biosignal information (S140). The health index may include numerical information such as the pulse rate, PPG, and respiration rate per unit time, and numerical information or normal/abnormal information according to the prestored calculation and analysis algorithm based on the received information. The display apparatus 200 may display a user's real-time health condition as the user's health index (S160).

The display apparatus 200 may extract the pulse information from the received information, and obtain a user's stress index as the health index from the pulse information. The pulse rate per unit time may be measured by a known method from the biosignal sensed by the 3D glasses 100, and accordingly the user's stress index is determined. For example, if the pulse rate is high, it means a user is in an excited state and accordingly a user's stress index rises. If the pulse rate is low, it means a user is in a relaxed state and accordingly a user's stress index may fall.

The display apparatus 200 monitors a user's health index which changes before viewing and while viewing a 3D image, and controls a display state according to the obtained health index (S150). The control method of the display apparatus 200 according to the obtained health index may include at least one of displaying an alarm, suspending play of the 3D content, adjusting 3D depth information, converting to a 2D mode and recommending a content corresponding to the health index.

The display apparatus 200 may inform a user of his/her real-time health condition by displaying the obtained health index. The example of displaying the health index is the same as that which has been described with reference to FIG. 4.

Figure 6:
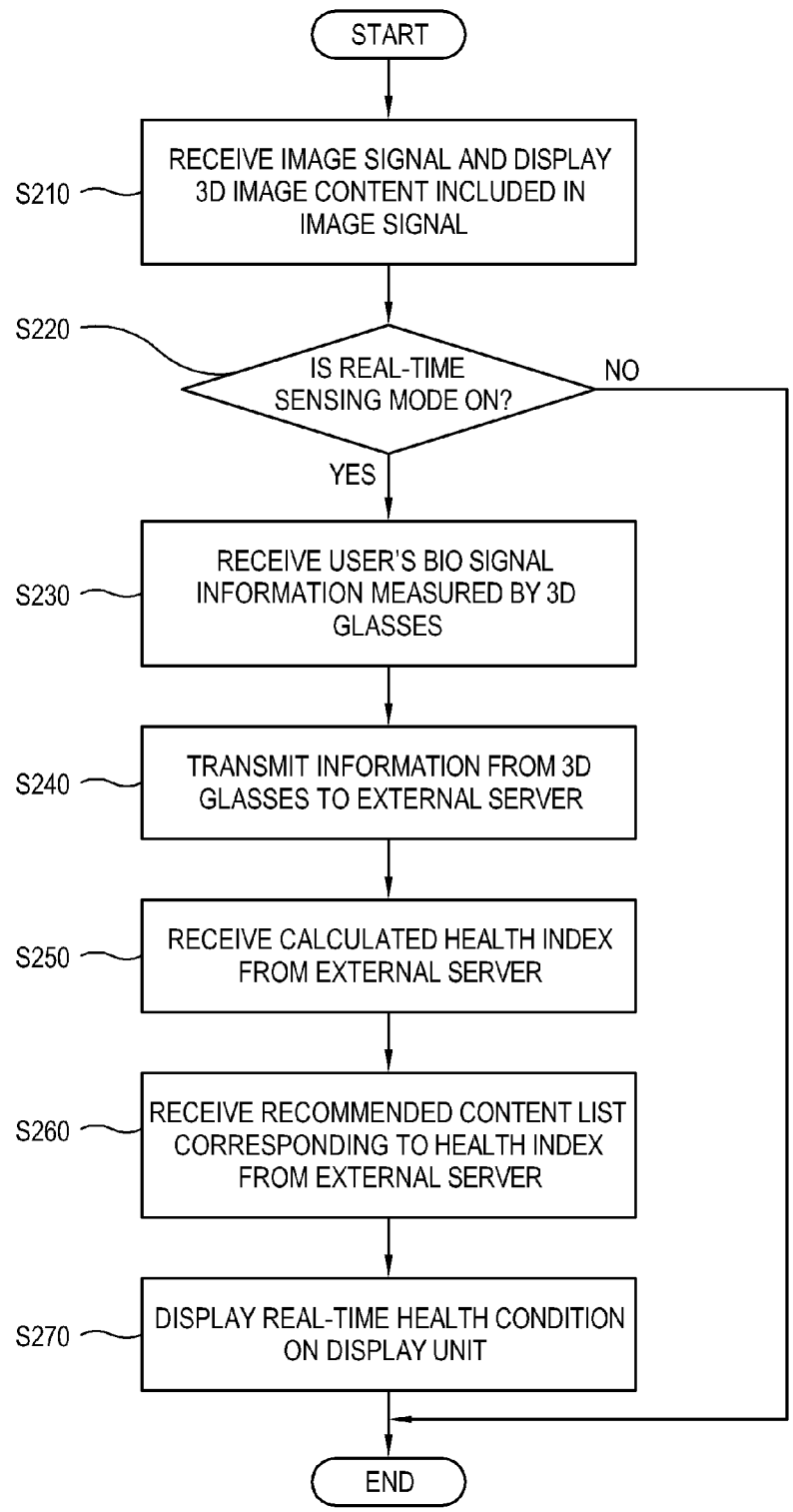
FIG. 6 is a second control flowchart of the display apparatus according to an exemplary embodiment.

FIG. 6 is a second control flowchart of the display apparatus 200 according to an exemplary embodiment.

The display apparatus 200 according to the present exemplary embodiment receives an image signal and displays 3D image content included in the image signal (S210). If the real-time sensing mode of the biosignal is set, the display apparatus 200 receives user's biosignal information measured by the 3D glasses 100 worn by a user (S230).

The display apparatus 200 transmit to the external server 300 the received user's biosignal information (S240). Upon receiving the information, the external server 300 analyzes the information and calculates the health index, and the display apparatus 200 receives in real-time the health index calculated by the external server 300. The method of receiving the biosignal from the external server 300 and calculating the health index is the same as that which has been described above.

The display apparatus 200 may receive a recommended content list corresponding to the health index from the external server 300 (S250). The received recommended content list may be displayed on the display unit 230 (S260), and the proper content viewing according to a user's current health condition may be offered.

In the above-described exemplary embodiment, the display apparatus 200 receives the biosignal information from the 3D glasses 100 and transmits the biosignal information to the external server 300 which calculates the health index based on the biosignal information. Alternatively, the external server 300 may receive the biosignal information from the 3D glasses 100 instead of from the display apparatus 200. In which case, the external server 300 calculates the health index based on the biosignal information received from the 3D glasses 100 and transmits the health index to the display apparatus 200.

As described above, a user health monitoring system, a display apparatus and a control method thereof according to an exemplary embodiment monitors in real-time a user's health condition through a biosignal of a user who is viewing a 3D image and controls a 3D display state according to the user's health condition to thereby protect a user's health.

Although a few exemplary embodiments have been shown and described, it will be appreciated by those skilled in the art that changes may be made in these exemplary embodiments without departing from the principles and spirit of the inventive concept, the range of which is defined in the appended claims and their equivalents.

What is claimed is:

1. A user health monitoring system comprising:
three-dimensional (3D) glasses which view a 3D image, obtain biosignal information of a user and transmit the biosignal information; and
a 3D display apparatus which displays the 3D image, receives the biosignal information transmitted by the 3D glasses, obtains a health index of the user by using the biosignal information and controls a display state according to the health index,
wherein the 3D display apparatus controls the display state by at least one of suspending play of 3D image content based on a numerical value of the health index, adjusting 3D depth information based on a numerical value of the health index, converting to a two-dimensional mode according to a numerical value of the health index, and recommending image content corresponding to a numerical value of the health index.

2. The user health monitoring system according to claim 1, wherein the 3D glasses comprise a pulse sensor to sense pulse information of the user and transmit the pulse information in the biosignal information to the 3D display apparatus.

3. The user health monitoring system according to claim 1, wherein the 3D glasses comprise a pulse sensor which is installed in a temple of the 3D glasses.

4. The user health monitoring system according to claim 1, wherein the 3D display apparatus controls the display state by displaying an alarm notification according to a numerical value of the health index.

5. The user health monitoring system according to claim 1, wherein the 3D display apparatus extracts pulse information from the biosignal information, and obtains a stress index of the user as the health index, from the pulse information.

6. The user health monitoring system according to claim 1, wherein the biosignal information comprises at least one of pulse information, photoplethysmography information, galvanic skin reflex information, skin conductivity information, electroencephalogram information, facial muscular motion information, and respiration information.

7. The user health monitoring system according to claim 1, further comprising an auxiliary electrode which measures at least one of electroencephalogram, electromyogram, and facial muscular motion, wherein the auxiliary electrode is connected to the 3D glasses, and a measurement result of the auxiliary electrode is included in the biological signal information transmitted to the 3D glasses.

8. The user health monitoring system according to claim 1, further comprising an external server which receives the biosignal information from the 3D display apparatus, determines the health index by analyzing the biosignal information, and transmits the health index to the 3D display apparatus.

9. The user health monitoring system according to claim 1, further comprising an external server which receives the biosignal information from the 3D display apparatus, determines the health index by analyzing the biosignal information, and transmits a recommended content list corresponding to the health index to the 3D display apparatus.

10. The user health monitoring system according to claim 1, wherein the 3D display apparatus displays a real-time health condition of the user as the health index.

11. A three-dimensional (3D) display apparatus comprising:
an image signal receiver which receives an image signal comprising three-dimensional (3D) image content;

an image processor which processes the image signal to be displayed;

a display unit which displays thereon the 3D image content included in the processed image signal;

a biosignal receiver which receives biosignal information of a user sensed by 3D glasses worn by the user to view the 3D image content; and a controller which controls the biosignal receiver to receive the biosignal information, obtains a health index of the user by using the biosignal information and controls a display state of the display unit according to the health index, wherein the controller controls the display state by at least one of suspending play of 3D image content based on a numerical value of the health index, adjusting 3D depth information based on a numerical value of the health index, converting to a two-dimensional mode according to a numerical value of the health index, and recommending image content corresponding to a numerical value of the health index.

12. The 3D display apparatus according to claim 11, wherein the controller controls the display state by displaying an alarm notification according to a numerical value of the health index.

13. The 3D display apparatus according to claim 11, wherein the controller extracts pulse information from the biosignal information and obtains a stress index of the user as the health index, from the pulse information.

14. The 3D display apparatus according to claim 11, wherein the biosignal information comprises at least one of pulse information, photoplethysmography information, galvanic skin reflex information, skin conductivity information, electroencephalogram information, facial muscular motion information, and respiration information.

15. The 3D display apparatus according to claim 11, wherein the controller displays on the display unit a real-time health condition of the user as the health index.

16. The 3D display apparatus according to claim 11, wherein the controller controls a transmission of the biosignal information to an external server, and a reception of the health index which is determined by analyzing the biosignal information in the external server.

17. The 3D display apparatus according to claim 11, wherein the controller controls a transmission of the biosignal information to an external server and a reception of a recommended content list corresponding to the health index which is determined by analyzing the biosignal information in the external server.

18. The 3D display apparatus according to claim 11, wherein the biosignal receiver receives the biosignal information from the 3D glasses by one of communication methods comprising Wi-Fi, Bluetooth, Zigbee, and ultra wideband.

19. A control method of a three-dimensional (3D) display apparatus, the control method comprising:

receiving an image signal and displaying on a display unit of the 3D display apparatus 3D image content comprised in the image signal;

receiving biosignal information of a user sensed by 3D glasses which are worn by the user to view the 3D image content;

obtaining a health index of the user by using the biosignal information; and controlling a display state of the display unit according to the health index, wherein the controlling the display state comprises at least one of suspending play of 3D image content based on a numerical value of the health index, adjusting 3D depth information based on a numerical value of the health index, converting to a two-dimensional mode according to a numerical value of the health index, and recommending image content corresponding to a numerical value of the health index.

20. The control method according to claim 19, wherein the controlling the display state comprises displaying an alarm notification according to a numerical value of the health index.

21. The control method according to claim 19, wherein the obtaining the health index comprises extracting pulse information from the biosignal information, and obtaining a stress index of the user as the health index from the pulse information.

22. The control method according to claim 19, wherein the biosignal information comprises at least one of pulse information, photoplethysmography information, galvanic skin reflex information, skin conductivity information, electroencephalogram information, facial muscular motion information, and respiration information.

23. The control method according to claim 19, further comprising displaying on the display unit a real-time health condition of the user as the health index.

24. The control method according to claim 19, further comprising transmitting the biosignal information to an external server, and receiving from the external server the health index determined by analyzing the biosignal information.

25. The control method according to claim 19, further comprising transmitting the biosignal information to an external server, and receiving from the external server a recommended content list corresponding to the health index determined by analyzing the biosignal information.

26. The control method according to claim 19, wherein the receiving the biosignal information comprises receiving the biosignal information from the 3D glasses by one of communication methods comprising Wi-Fi, Bluetooth, Zigbee, and ultra wideband.

* * * * *